United States Patent
Stevenson et al.

(10) Patent No.: US 9,186,144 B2
(45) Date of Patent: Nov. 17, 2015

(54) BUTTRESS SUPPORT DESIGN FOR EEA ANVIL

(71) Applicant: Covidien LP, Mansfield, MA (US)

(72) Inventors: Richard Stevenson, Colchester, CT (US); Thomas Casasanta, Jr., Kensington, CT (US); Sally Carter, Nashua, NH (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/628,966

(22) Filed: Feb. 23, 2015

(65) Prior Publication Data

US 2015/0164503 A1 Jun. 18, 2015

Related U.S. Application Data

(63) Continuation of application No. 13/358,544, filed on Jan. 26, 2012, now Pat. No. 9,010,612.

(51) Int. Cl.
*A61B 17/072* (2006.01)
*A61B 17/115* (2006.01)
*A61B 17/11* (2006.01)

(52) U.S. Cl.
CPC ....... *A61B 17/07292* (2013.01); *A61B 17/1155* (2013.01); *A61B 2017/07214* (2013.01); *A61B 2017/07257* (2013.01); *A61B 2017/1132* (2013.01)

(58) Field of Classification Search
CPC ............ A61B 17/068; A61B 17/0686; A61B 17/072; A61B 17/07207; A61B 17/07292; A61B 17/07214
USPC ........... 227/19, 175.1, 176.1, 180.1; 606/139, 606/143, 151, 153, 219
See application file for complete search history.

(56) References Cited

U.S. PATENT DOCUMENTS 3,054,406 A 9/1962 Usher
3,079,606 A 3/1963 Bobrov et al.
(Continued)

FOREIGN PATENT DOCUMENTS

CA 2 667 434 A1 5/2008
DE 19924311 A1 11/2000
(Continued)

OTHER PUBLICATIONS

European Search Report corresponding to EP 05 02 2585.3, completed Jan. 25, 2006 and mailed Feb. 3, 2006; (4 pp).
(Continued)

*Primary Examiner* — Scott A. Smith

(57) ABSTRACT

An apparatus for joining two hollow organ sections with an annular array of surgical staples includes a staple cartridge, an anvil, a buttress member, and a buttress mount. In particular, the staple cartridge includes a plurality of surgical staples in an annular array. The anvil includes an anvil member and a shaft extending therefrom. The anvil member defines a plurality of staple pockets for deforming the surgical staples. The anvil is movable relative to the staple cartridge component between spaced apart and approximated positions to adjustably clamp tissue between the staple cartridge and the anvil. The buttress member is concentrically aligned with the plurality of staple pockets defined in the anvil member. The buttress mount is detachably secured with the shaft of the anvil. The buttress mount includes at least one support member radially extending outward to secure the buttress member to the anvil member.

8 Claims, 11 Drawing Sheets

(56) References Cited

U.S. PATENT DOCUMENTS

| | | | |
|---|---|---|---|
| 3,124,136 | A | 3/1964 | Usher |
| 3,364,200 | A | 1/1968 | Ashton et al. |
| 3,490,675 | A | 1/1970 | Green et al. |
| 3,499,591 | A | 3/1970 | Green |
| 3,939,068 | A | 2/1976 | Wendt et al. |
| 3,948,666 | A | 4/1976 | Kitanishi et al. |
| 4,064,062 | A | 12/1977 | Yurko |
| 4,166,800 | A | 9/1979 | Fong |
| 4,282,236 | A | 8/1981 | Broom |
| 4,347,847 | A | 9/1982 | Usher |
| 4,354,628 | A | 10/1982 | Green |
| 4,416,698 | A | 11/1983 | McCorsley, III |
| 4,429,695 | A | 2/1984 | Green |
| 4,452,245 | A | 6/1984 | Usher |
| 4,473,077 | A | 9/1984 | Noiles et al. |
| 4,576,167 | A | 3/1986 | Noiles |
| 4,592,354 | A * | 6/1986 | Rothfuss .................. 227/179.1 |
| 4,605,730 | A | 8/1986 | Shalaby et al. |
| 4,626,253 | A | 12/1986 | Broadnax, Jr. |
| 4,646,745 | A | 3/1987 | Noiles |
| 4,655,221 | A | 4/1987 | Devereux |
| 4,834,090 | A | 5/1989 | Moore |
| 4,838,884 | A | 6/1989 | Dumican et al. |
| 4,927,640 | A | 5/1990 | Dahlinder et al. |
| 4,930,674 | A | 6/1990 | Barak |
| 5,002,551 | A | 3/1991 | Linsky et al. |
| 5,005,749 | A | 4/1991 | Aranyi |
| 5,014,899 | A | 5/1991 | Presty et al. |
| 5,040,715 | A | 8/1991 | Green et al. |
| 5,057,334 | A | 10/1991 | Vail |
| 5,065,929 | A | 11/1991 | Schulze et al. |
| 5,119,983 | A | 6/1992 | Green et al. |
| 5,162,430 | A | 11/1992 | Rhee et al. |
| 5,205,459 | A | 4/1993 | Brinkerhoff et al. |
| 5,250,058 | A | 10/1993 | Miller et al. |
| 5,263,629 | A | 11/1993 | Trumbull et al. |
| 5,307,976 | A | 5/1994 | Olson et al. |
| 5,312,023 | A | 5/1994 | Green et al. |
| 5,314,471 | A | 5/1994 | Brauker et al. |
| 5,318,221 | A | 6/1994 | Green et al. |
| 5,324,775 | A | 6/1994 | Rhee et al. |
| 5,326,013 | A | 7/1994 | Green et al. |
| 5,332,142 | A | 7/1994 | Robinson et al. |
| 5,344,454 | A | 9/1994 | Clarke et al. |
| 5,346,501 | A | 9/1994 | Regula et al. |
| 5,392,979 | A | 2/1995 | Green et al. |
| 5,397,324 | A | 3/1995 | Carroll et al. |
| 5,410,016 | A | 4/1995 | Hubbell et al. |
| 5,425,745 | A | 6/1995 | Green et al. |
| 5,441,193 | A | 8/1995 | Gravener |
| 5,441,507 | A | 8/1995 | Wilk |
| 5,443,198 | A | 8/1995 | Viola et al. |
| 5,468,253 | A | 11/1995 | Bezwada et al. |
| 5,484,913 | A | 1/1996 | Stilwell et al. |
| 5,503,638 | A | 4/1996 | Cooper et al. |
| 5,514,379 | A | 5/1996 | Weissleder et al. |
| 5,542,594 | A | 8/1996 | McKean et al. |
| 5,543,441 | A | 8/1996 | Rhee et al. |
| 5,549,628 | A | 8/1996 | Cooper et al. |
| 5,550,187 | A | 8/1996 | Rhee et al. |
| 5,575,803 | A | 11/1996 | Cooper et al. |
| 5,588,579 | A | 12/1996 | Schnut et al. |
| 5,653,756 | A | 8/1997 | Clarke et al. |
| 5,683,809 | A | 11/1997 | Freeman et al. |
| 5,690,675 | A | 11/1997 | Sawyer et al. |
| 5,702,409 | A | 12/1997 | Rayburn et al. |
| 5,752,965 | A | 5/1998 | Francis et al. |
| 5,752,974 | A | 5/1998 | Rhee et al. |
| 5,762,256 | A | 6/1998 | Mastri et al. |
| 5,766,188 | A | 6/1998 | Igaki |
| 5,769,892 | A | 6/1998 | Kingwell |
| 5,782,396 | A | 7/1998 | Mastri et al. |
| 5,799,857 | A | 9/1998 | Robertson et al. |
| 5,810,855 | A | 9/1998 | Rayburn et al. |
| 5,814,057 | A | 9/1998 | Oi et al. |
| 5,819,350 | A | 10/1998 | Wang |
| 5,833,695 | A | 11/1998 | Yoon |
| 5,843,096 | A | 12/1998 | Igaki et al. |
| 5,874,500 | A | 2/1999 | Rhee et al. |
| 5,895,412 | A | 4/1999 | Tucker |
| 5,895,415 | A | 4/1999 | Chow et al. |
| 5,902,312 | A | 5/1999 | Frater et al. |
| 5,908,427 | A | 6/1999 | McKean et al. |
| 5,915,616 | A | 6/1999 | Viola et al. |
| 5,931,847 | A | 8/1999 | Bittner et al. |
| 5,964,774 | A | 10/1999 | McKean et al. |
| 5,997,895 | A | 12/1999 | Narotam et al. |
| 6,019,791 | A | 2/2000 | Wood |
| 6,030,392 | A | 2/2000 | Dakov |
| 6,032,849 | A | 3/2000 | Mastri et al. |
| 6,045,560 | A | 4/2000 | McKean et al. |
| 6,053,390 | A | 4/2000 | Green et al. |
| 6,063,097 | A | 5/2000 | Oi et al. |
| 6,080,169 | A | 6/2000 | Turtel |
| 6,093,557 | A | 7/2000 | Pui et al. |
| 6,099,551 | A | 8/2000 | Gabbay |
| 6,149,667 | A | 11/2000 | Hovland et al. |
| 6,152,943 | A | 11/2000 | Sawhney |
| 6,155,265 | A | 12/2000 | Hammerslag |
| 6,156,677 | A | 12/2000 | Brown Reed et al. |
| 6,165,201 | A | 12/2000 | Sawhney et al. |
| 6,179,862 | B1 | 1/2001 | Sawhney |
| 6,210,439 | B1 | 4/2001 | Firmin et al. |
| 6,214,020 | B1 | 4/2001 | Mulhauser et al. |
| 6,241,139 | B1 | 6/2001 | Milliman et al. |
| 6,258,107 | B1 | 7/2001 | Balazs et al. |
| 6,267,772 | B1 | 7/2001 | Mulhauser et al. |
| 6,273,897 | B1 | 8/2001 | Dalessandro et al. |
| 6,280,453 | B1 | 8/2001 | Kugel et al. |
| 6,299,631 | B1 | 10/2001 | Shalaby |
| 6,309,569 | B1 | 10/2001 | Farrar et al. |
| 6,312,457 | B1 | 11/2001 | DiMatteo et al. |
| 6,312,474 | B1 | 11/2001 | Francis et al. |
| 6,325,810 | B1 | 12/2001 | Hamilton et al. |
| 6,399,362 | B1 | 6/2002 | Pui et al. |
| 6,436,030 | B2 | 8/2002 | Rehil |
| 6,454,780 | B1 | 9/2002 | Wallace |
| 6,461,368 | B2 | 10/2002 | Fogarty et al. |
| 6,500,777 | B1 | 12/2002 | Wiseman et al. |
| 6,503,257 | B2 | 1/2003 | Grant et al. |
| 6,503,259 | B2 | 1/2003 | Huxel et al. |
| 6,514,283 | B2 | 2/2003 | DiMatteo et al. |
| 6,514,534 | B1 | 2/2003 | Sawhney |
| 6,517,566 | B1 | 2/2003 | Hovland et al. |
| 6,551,356 | B2 | 4/2003 | Rousseau |
| 6,566,406 | B1 | 5/2003 | Pathak et al. |
| 6,590,095 | B1 | 7/2003 | Schleicher et al. |
| 6,592,597 | B2 | 7/2003 | Grant et al. |
| 6,605,294 | B2 | 8/2003 | Sawhney |
| 6,627,749 | B1 | 9/2003 | Kumar |
| 6,638,285 | B2 | 10/2003 | Gabbay |
| 6,652,594 | B2 | 11/2003 | Francis et al. |
| 6,656,193 | B2 | 12/2003 | Grant et al. |
| 6,656,200 | B2 | 12/2003 | Li et al. |
| 6,669,735 | B1 | 12/2003 | Pelissier |
| 6,673,093 | B1 | 1/2004 | Sawhney |
| 6,677,258 | B2 | 1/2004 | Carroll et al. |
| 6,685,714 | B2 | 2/2004 | Rousseau |
| 6,702,828 | B2 | 3/2004 | Whayne |
| 6,703,047 | B2 | 3/2004 | Sawhney et al. |
| 6,704,210 | B1 | 3/2004 | Myers |
| 6,723,114 | B2 | 4/2004 | Shalaby |
| 6,726,706 | B2 | 4/2004 | Dominguez |
| 6,736,823 | B2 | 5/2004 | Darois et al. |
| 6,736,854 | B2 | 5/2004 | Vadurro et al. |
| 6,746,458 | B1 | 6/2004 | Cloud |
| 6,746,869 | B2 | 6/2004 | Pui et al. |
| 6,764,720 | B2 | 7/2004 | Pui et al. |
| 6,773,458 | B1 | 8/2004 | Brauker et al. |
| 6,818,018 | B1 | 11/2004 | Sawhney |
| 6,896,684 | B2 | 5/2005 | Monassevitch et al. |
| 6,927,315 | B1 | 8/2005 | Heinecke et al. |
| 6,939,358 | B2 | 9/2005 | Palacios et al. |
| 6,946,196 | B2 | 9/2005 | Foss |

(56) References Cited

U.S. PATENT DOCUMENTS

| | | | |
|---|---|---|---|
| 6,959,851 B2 | 11/2005 | Heinrich | |
| 7,009,034 B2 | 3/2006 | Pathak et al. | |
| 7,060,087 B2 | 6/2006 | DiMatteo et al. | |
| 7,087,065 B2 | 8/2006 | Ulmsten et al. | |
| 7,108,701 B2 | 9/2006 | Evens et al. | |
| 7,128,253 B2 | 10/2006 | Mastri et al. | |
| 7,128,748 B2 * | 10/2006 | Mooradian et al. | 606/151 |
| 7,141,055 B2 | 11/2006 | Abrams et al. | |
| 7,147,138 B2 | 12/2006 | Shelton, IV | |
| 7,160,299 B2 | 1/2007 | Baily | |
| 7,232,449 B2 | 6/2007 | Sharkawy et al. | |
| 7,241,300 B2 | 7/2007 | Sharkawy et al. | |
| 7,247,338 B2 | 7/2007 | Pui et al. | |
| 7,279,322 B2 | 10/2007 | Pui et al. | |
| 7,307,031 B2 | 12/2007 | Carroll et al. | |
| 7,311,720 B2 | 12/2007 | Mueller et al. | |
| 7,347,850 B2 | 3/2008 | Sawhney | |
| 7,377,928 B2 | 5/2008 | Zubik et al. | |
| 7,434,717 B2 | 10/2008 | Shelton, IV et al. | |
| 7,438,209 B1 | 10/2008 | Hess et al. | |
| 7,498,063 B2 | 3/2009 | Pui et al. | |
| 7,547,312 B2 * | 6/2009 | Bauman et al. | 606/151 |
| 7,559,937 B2 | 7/2009 | de la Torre et al. | |
| 7,594,921 B2 | 9/2009 | Browning | |
| 7,595,392 B2 | 9/2009 | Kumar et al. | |
| 7,604,151 B2 | 10/2009 | Hess et al. | |
| 7,611,494 B2 | 11/2009 | Campbell et al. | |
| 7,635,073 B2 | 12/2009 | Heinrich | |
| 7,649,089 B2 | 1/2010 | Kumar et al. | |
| 7,662,801 B2 | 2/2010 | Kumar et al. | |
| 7,665,646 B2 | 2/2010 | Prommersberger | |
| 7,666,198 B2 | 2/2010 | Suyker et al. | |
| 7,669,747 B2 | 3/2010 | Weisenburgh, II et al. | |
| 7,717,313 B2 | 5/2010 | Criscuolo et al. | |
| 7,722,642 B2 | 5/2010 | Williamson, IV et al. | |
| 7,744,627 B2 | 6/2010 | Orban, III et al. | |
| 7,776,060 B2 | 8/2010 | Mooradian et al. | |
| 7,793,813 B2 | 9/2010 | Bettuchi | |
| 7,799,026 B2 | 9/2010 | Schechter et al. | |
| 7,823,592 B2 * | 11/2010 | Bettuchi et al. | 128/898 |
| 7,824,420 B2 | 11/2010 | Eldridge et al. | |
| 7,845,533 B2 | 12/2010 | Marczyk et al. | |
| 7,845,536 B2 | 12/2010 | Viola et al. | |
| 7,846,149 B2 | 12/2010 | Jankowski | |
| 7,892,247 B2 | 2/2011 | Conston et al. | |
| 7,909,224 B2 | 3/2011 | Prommersberger | |
| 7,909,837 B2 | 3/2011 | Crews et al. | |
| 7,938,307 B2 | 5/2011 | Bettuchi | |
| 7,942,890 B2 | 5/2011 | D'Agostino et al. | |
| 7,950,561 B2 | 5/2011 | Aranyi | |
| 7,951,166 B2 | 5/2011 | Orban, III et al. | |
| 7,951,248 B1 | 5/2011 | Fallis et al. | |
| 7,967,179 B2 | 6/2011 | Olson et al. | |
| 7,975,895 B2 * | 7/2011 | Milliman | 227/179.1 |
| 7,988,027 B2 | 8/2011 | Olson et al. | |
| 8,011,550 B2 | 9/2011 | Aranyi et al. | |
| 8,011,555 B2 | 9/2011 | Tarinelli et al. | |
| 8,016,177 B2 | 9/2011 | Bettuchi et al. | |
| 8,016,178 B2 | 9/2011 | Olson et al. | |
| 8,028,883 B2 | 10/2011 | Stopek | |
| 8,033,483 B2 | 10/2011 | Fortier et al. | |
| 8,038,045 B2 | 10/2011 | Bettuchi et al. | |
| 8,062,330 B2 | 11/2011 | Prommersberger et al. | |
| 8,083,119 B2 | 12/2011 | Prommersberger | |
| 8,123,766 B2 | 2/2012 | Bauman et al. | |
| 8,123,767 B2 | 2/2012 | Bauman et al. | |
| 8,146,791 B2 * | 4/2012 | Bettuchi et al. | 227/179.1 |
| 8,152,777 B2 | 4/2012 | Campbell et al. | |
| 8,157,149 B2 | 4/2012 | Olson et al. | |
| 8,157,151 B2 | 4/2012 | Ingmanson et al. | |
| 8,167,895 B2 * | 5/2012 | D'Agostino et al. | 606/139 |
| 8,186,558 B2 | 5/2012 | Sapienza | |
| 8,192,460 B2 | 6/2012 | Orban, III et al. | |
| 8,210,414 B2 | 7/2012 | Bettuchi et al. | |
| 8,225,799 B2 * | 7/2012 | Bettuchi | 128/898 |
| 8,225,981 B2 | 7/2012 | Criscuolo et al. | |
| 8,231,043 B2 | 7/2012 | Tarinelli et al. | |
| 8,235,273 B2 | 8/2012 | Olson et al. | |
| 8,245,901 B2 | 8/2012 | Stopek | |
| 8,256,654 B2 | 9/2012 | Bettuchi et al. | |
| 8,257,391 B2 | 9/2012 | Orban, III et al. | |
| 8,276,800 B2 | 10/2012 | Bettuchi | |
| 8,286,849 B2 | 10/2012 | Bettuchi | |
| 8,308,042 B2 | 11/2012 | Aranyi | |
| 8,308,045 B2 | 11/2012 | Bettuchi et al. | |
| 8,308,046 B2 | 11/2012 | Prommersberger | |
| 8,312,885 B2 | 11/2012 | Bettuchi et al. | |
| 8,313,014 B2 | 11/2012 | Bettuchi | |
| 8,348,126 B2 | 1/2013 | Olson et al. | |
| 8,348,130 B2 | 1/2013 | Shah et al. | |
| 8,365,972 B2 | 2/2013 | Aranyi et al. | |
| 8,371,491 B2 | 2/2013 | Huitema et al. | |
| 8,371,492 B2 | 2/2013 | Aranyi et al. | |
| 8,371,493 B2 | 2/2013 | Aranyi et al. | |
| 8,393,514 B2 | 3/2013 | Shelton, IV et al. | |
| 8,408,440 B2 | 4/2013 | Olson et al. | |
| 8,413,871 B2 | 4/2013 | Racenet et al. | |
| 8,424,742 B2 | 4/2013 | Bettuchi | |
| 8,453,652 B2 | 6/2013 | Stopek | |
| 8,453,904 B2 | 6/2013 | Eskaros et al. | |
| 8,453,909 B2 | 6/2013 | Olson et al. | |
| 8,453,910 B2 | 6/2013 | Bettuchi et al. | |
| 8,464,925 B2 | 6/2013 | Hull et al. | |
| 8,474,677 B2 | 7/2013 | Woodard, Jr. et al. | |
| 8,479,968 B2 | 7/2013 | Hodgkinson et al. | |
| 8,485,414 B2 | 7/2013 | Criscuolo et al. | |
| 8,496,683 B2 | 7/2013 | Prommersberger et al. | |
| 8,511,533 B2 * | 8/2013 | Viola et al. | 227/179.1 |
| 8,512,402 B2 | 8/2013 | Marczyk et al. | |
| 8,529,600 B2 | 9/2013 | Woodard, Jr. et al. | |
| 8,540,131 B2 | 9/2013 | Swayze | |
| 8,551,138 B2 | 10/2013 | Orban, III et al. | |
| 8,556,918 B2 | 10/2013 | Bauman et al. | |
| 8,561,873 B2 | 10/2013 | Ingmanson et al. | |
| 8,584,920 B2 | 11/2013 | Hodgkinson | |
| 8,590,762 B2 | 11/2013 | Hess et al. | |
| 8,616,430 B2 | 12/2013 | Stopek et al. | |
| 8,631,989 B2 | 1/2014 | Aranyi et al. | |
| 8,668,129 B2 | 3/2014 | Olson | |
| 8,684,250 B2 | 4/2014 | Bettuchi et al. | |
| 8,757,466 B2 | 6/2014 | Olson et al. | |
| 8,789,737 B2 | 7/2014 | Hodgkinson et al. | |
| 8,820,606 B2 | 9/2014 | Hodgkinson | |
| 8,870,050 B2 | 10/2014 | Hodgkinson | |
| 8,939,344 B2 | 1/2015 | Olson et al. | |
| 8,967,448 B2 * | 3/2015 | Carter et al. | 227/176.1 |
| 9,005,243 B2 | 4/2015 | Stopek et al. | |
| 9,010,606 B2 | 4/2015 | Aranyi et al. | |
| 9,010,608 B2 * | 4/2015 | Casasanta et al. | 227/176.1 |
| 9,010,609 B2 * | 4/2015 | Carter et al. | 227/176.1 |
| 9,010,610 B2 | 4/2015 | Hodgkinson | |
| 9,010,612 B2 | 4/2015 | Stevenson et al. | |
| 9,016,543 B2 | 4/2015 | Stopek et al. | |
| 9,016,544 B2 | 4/2015 | Hodgkinson et al. | |
| 2002/0028243 A1 | 3/2002 | Masters | |
| 2002/0086990 A1 | 7/2002 | Kumar et al. | |
| 2002/0091397 A1 | 7/2002 | Chen | |
| 2003/0065345 A1 | 4/2003 | Weadock | |
| 2003/0078209 A1 | 4/2003 | Schmidt | |
| 2003/0083676 A1 | 5/2003 | Wallace | |
| 2003/0120284 A1 | 6/2003 | Palacios et al. | |
| 2003/0181927 A1 | 9/2003 | Wallace | |
| 2003/0183671 A1 | 10/2003 | Mooradian et al. | |
| 2003/0208231 A1 | 11/2003 | Williamson et al. | |
| 2004/0107006 A1 | 6/2004 | Francis et al. | |
| 2004/0254590 A1 | 12/2004 | Hoffman et al. | |
| 2004/0260315 A1 | 12/2004 | Dell et al. | |
| 2005/0002981 A1 | 1/2005 | Lahtinen et al. | |
| 2005/0021085 A1 | 1/2005 | Abrams et al. | |
| 2005/0059996 A1 | 3/2005 | Bauman et al. | |
| 2005/0059997 A1 | 3/2005 | Bauman et al. | |
| 2005/0070929 A1 | 3/2005 | Dalessandro et al. | |
| 2005/0118435 A1 | 6/2005 | DeLucia et al. | |
| 2005/0131225 A1 | 6/2005 | Kumar et al. | |

(56) References Cited

U.S. PATENT DOCUMENTS

| | | |
|---|---|---|
| 2005/0143756 A1 | 6/2005 | Jankowski |
| 2005/0149073 A1 | 7/2005 | Arani et al. |
| 2005/0154093 A1 | 7/2005 | Kwon et al. |
| 2005/0245965 A1* | 11/2005 | Orban, III et al. ............ 606/214 |
| 2006/0004407 A1 | 1/2006 | Hiles et al. |
| 2006/0008505 A1 | 1/2006 | Brandon |
| 2006/0093672 A1 | 5/2006 | Kumar et al. |
| 2006/0121266 A1 | 6/2006 | Fandel et al. |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0054880 A1 | 3/2007 | Saferstein et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0213522 A1 | 9/2007 | Harris et al. |
| 2007/0237741 A1 | 10/2007 | Figuly et al. |
| 2007/0237742 A1 | 10/2007 | Figuly et al. |
| 2007/0243227 A1 | 10/2007 | Gertner |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0164440 A1 | 7/2008 | Maase et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0194805 A1 | 8/2008 | Vignon et al. |
| 2008/0200949 A1 | 8/2008 | Hiles et al. |
| 2008/0214695 A1 | 9/2008 | Pathak et al. |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0220560 A1 | 9/2009 | Wan et al. |
| 2009/0263441 A1 | 10/2009 | McKay |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0065660 A1 | 3/2010 | Hull et al. |
| 2010/0072254 A1 | 3/2010 | Aranyi et al. |
| 2010/0096481 A1 | 4/2010 | Hull et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0203151 A1 | 8/2010 | Hiraoka |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0082427 A1 | 4/2011 | Golzarian et al. |
| 2011/0087279 A1 | 4/2011 | Shah et al. |
| 2011/0089375 A1 | 4/2011 | Chan et al. |
| 2011/0215132 A1 | 9/2011 | Aranyi et al. |
| 2011/0293690 A1 | 12/2011 | Griffin et al. |
| 2012/0074199 A1 | 3/2012 | Olson et al. |
| 2012/0080336 A1 | 4/2012 | Shelton, IV et al. |
| 2012/0156289 A1 | 6/2012 | Blaskovich et al. |
| 2012/0187179 A1 | 7/2012 | Gleiman |
| 2012/0241499 A1 | 9/2012 | Baxter, III et al. |
| 2012/0273547 A1 | 11/2012 | Hodgkinson et al. |
| 2013/0037596 A1 | 2/2013 | Bear et al. |
| 2013/0105548 A1 | 5/2013 | Hodgkinson et al. |
| 2013/0105553 A1 | 5/2013 | Racenet et al. |
| 2013/0112732 A1 | 5/2013 | Aranyi et al. |
| 2013/0112733 A1 | 5/2013 | Aranyi et al. |
| 2013/0146641 A1 | 6/2013 | Shelton, IV et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze et al. |
| 2013/0181031 A1 | 7/2013 | Olson et al. |
| 2013/0193186 A1 | 8/2013 | Racenet et al. |
| 2013/0193190 A1 | 8/2013 | Carter et al. |
| 2013/0193192 A1 | 8/2013 | Casasanta, Jr. et al. |
| 2013/0209659 A1 | 8/2013 | Racenet et al. |
| 2013/0221062 A1 | 8/2013 | Hodgkinson |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0277411 A1 | 10/2013 | Hodgkinson et al. |
| 2013/0306707 A1 | 11/2013 | Viola et al. |
| 2013/0310873 A1 | 11/2013 | Stopek et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0061281 A1 | 3/2014 | Hodgkinson |
| 2014/0084042 A1 | 3/2014 | Stopek et al. |
| 2014/0097224 A1 | 4/2014 | Prior |
| 2014/0117066 A1 | 5/2014 | Aranyi et al. |
| 2014/0130330 A1 | 5/2014 | Olson et al. |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |

(56) References Cited

U.S. PATENT DOCUMENTS

| | | |
|---|---|---|
| 2014/0158742 A1 | 6/2014 | Stopek et al. |
| 2014/0166721 A1 | 6/2014 | Stevenson et al. |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson et al. |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |

FOREIGN PATENT DOCUMENTS

| | | |
|---|---|---|
| EP | 0 327 022 A2 | 8/1989 |
| EP | 0 594 148 A1 | 4/1994 |
| EP | 0 667 119 A1 | 8/1995 |
| EP | 1 064 883 A1 | 1/2001 |
| EP | 1 256 317 A2 | 11/2002 |
| EP | 1 256 318 A1 | 11/2002 |
| EP | 1 520 525 A1 | 4/2005 |
| EP | 1 621 141 A2 | 2/2006 |
| EP | 1 702 570 A1 | 9/2006 |
| EP | 1 759 640 A2 | 3/2007 |
| EP | 1 815 804 A2 | 8/2007 |
| EP | 1 825 820 A1 | 8/2007 |
| EP | 1 929 958 A2 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 090 231 A1 | 8/2009 |
| EP | 2 090 244 A2 | 8/2009 |
| EP | 2 090 252 A2 | 8/2009 |
| EP | 2 198 787 A1 | 6/2010 |
| EP | 2 236 098 A2 | 10/2010 |
| EP | 2 236 099 A1 | 10/2010 |
| EP | 2 292 276 A2 | 3/2011 |
| EP | 2 311 386 A1 | 4/2011 |
| EP | 2 436 348 A1 | 4/2012 |
| EP | 2 462 880 A2 | 6/2012 |
| EP | 2 517 637 A1 | 10/2012 |
| EP | 2 586 380 A1 | 5/2013 |
| EP | 2 604 195 A1 | 6/2013 |
| EP | 2 604 197 A2 | 6/2013 |
| EP | 2 620 105 A1 | 7/2013 |
| EP | 2 620 106 A2 | 7/2013 |
| EP | 2 630 922 A1 | 8/2013 |
| EP | 2 644 125 A2 | 10/2013 |
| EP | 2 762 091 A2 | 8/2014 |
| JP | 2000-166933 A | 6/2000 |
| JP | 2002-202213 A | 7/2002 |
| JP | 2007-124166 A | 5/2007 |
| JP | 07124166 | 5/2007 |
| WO | 90/05489 A1 | 5/1990 |
| WO | 95/16221 A1 | 6/1995 |
| WO | 96/22055 A1 | 7/1996 |
| WO | 97/01989 A1 | 1/1997 |
| WO | 97/13463 A1 | 4/1997 |
| WO | 98/17180 A1 | 4/1998 |
| WO | 99/45849 A1 | 9/1999 |
| WO | 03/082126 A1 | 10/2003 |
| WO | 03/088845 A2 | 10/2003 |
| WO | 03/094743 A1 | 11/2003 |
| WO | 03/105698 A2 | 12/2003 |
| WO | 2005079675 A2 | 9/2005 |
| WO | 2006023578 A2 | 3/2006 |
| WO | 2006044490 A2 | 4/2006 |
| WO | 2006083748 A1 | 8/2006 |
| WO | 2007121579 A1 | 11/2007 |
| WO | 2008057281 A2 | 5/2008 |
| WO | 2008109125 A1 | 9/2008 |
| WO | 2010075298 A2 | 7/2010 |
| WO | 2011143183 A2 | 11/2011 |
| WO | 2012044848 A1 | 4/2012 |

OTHER PUBLICATIONS

European Search Report corresponding to EP 06 00 4598, completed Jun. 22, 2006; (2 pp).

European Search Report corresponding to EP 06 01 6962.0, completed Jan. 3, 2007 and mailed Jan. 11, 2007; (10 pp).

International Search Report corresponding to International Application No. PCT/US2005/036740, completed Feb. 20, 2007 and mailed Mar. 23, 2007; (8 pp).

International Search Report corresponding to International Application No. PCT/US2007/022713, completed Apr. 21, 2008 and mailed May 15, 2008; (1 p).

International Search Report corresponding to International Application No. PCT/US2008/002981, completed Jun. 9, 2008 and mailed Jun. 26, 2008; (2 pp).

European Search Report corresponding to EP 08 25 1779, completed Jul. 14, 2008 and mailed Jul. 23, 2008; (5 pp).

European Search Report corresponding to EP 08 25 1989.3, completed Mar. 11, 2010 and mailed Mar. 24, 2010; (6 pp).

European Search Report corresponding to EP 10 25 0639.1, completed Jun. 17, 2010 and mailed Jun. 28, 2010; (7 pp).

European Search Report corresponding to EP 10 25 0715.9, completed Jun. 30, 2010 and mailed Jul. 20, 2010; (3 pp).

European Search Report corresponding to EP 05 80 4382.9, completed Oct. 5, 2010 and mailed Oct. 12, 2010; (3 pp).

European Search Report corresponding to EP 10 25 1437.9, completed Nov. 22, 2010 and mailed Dec. 16, 2010; (3 pp).

European Search Report corresponding to EP 09 25 2897.5, completed Feb. 7, 2011 and mailed Feb. 15, 2011; (3 pp).

European Search Report corresponding to EP 10 25 0642.5, completed Mar. 25, 2011 and mailed Apr. 4, 2011; (4 pp).

European Search Report corresponding to EP 11 18 8309.6, completed Dec. 15, 2011 and mailed Jan. 12, 2012; (3 pp).

European Search Report corresponding to EP 12 15 2229.6, completed Feb. 23, 2012 and mailed Mar. 1, 2012; (4 pp).

European Search Report corresponding to EP 12 15 0511.9, completed Apr. 16, 2012 and mailed Apr. 24, 2012; (7 pp).

European Search Report corresponding to EP 12 15 2541.4, completed Apr. 23, 2012 and mailed May 3, 2012; (10 pp).

European Search Report corresponding to EP 12 16 5609.4, completed Jul. 5, 2012 and mailed Jul. 13, 2012; (8 pp).

European Search Report corresponding to EP 12 15 8861.0, completed Jul. 17, 2012 and mailed Jul. 24, 2012; (9 pp).

European Search Report corresponding to EP 12 16 5878.5, completed Jul. 24, 2012 and mailed Aug. 6, 2012; (8 pp).

Extended European Search Report corresponding to EP 12 19 1035.0, completed Jan. 11, 2013 and mailed Jan. 18, 2013; (7 pp).

Extended European Search Report corresponding to EP 12 18 6175.1, completed Jan. 15, 2013 and mailed Jan. 23, 2013; (7 pp).

Extended European Search Report corresponding to EP 12 19 1114.3, completed Jan. 23, 2013 and mailed Jan. 31, 2013; (10 pp).

Extended European Search Report corresponding to EP 12 19 2224.9, completed Mar. 14, 2013 and mailed Mar. 26, 2013; (8 pp).

Extended European Search Report corresponding to EP 12 19 6904.2, completed Mar. 28, 2013 and mailed Jul. 26, 2013; (8 pp).

Extended European Search Report corresponding to EP 12 19 6911.7, completed Apr. 18, 2013 and mailed Apr. 24, 2013; (8 pp).

Extended European Search Report corresponding to EP 07 00 5842.5, completed May 13, 2013 and mailed May 29, 2013; (7 pp).

Extended European Search Report corresponding to EP 12 19 8776.2, completed May 16, 2013 and mailed May 27, 2013; (8 pp).

Extended European Search Report corresponding to EP 12 19 8749.9, completed May 21, 2013 and mailed May 31, 2013; (8 pp).

Extended European Search Report corresponding to EP 13 15 6297.7, completed Jun. 4, 2013 and mailed Jun. 13, 2013l; (7 pp).

Extended European Search Report corresponding to EP 13 17 3985.6, completed Aug. 19, 2013 and mailed Aug. 28, 2013; (6 pp).

Extended European Search Report corresponding to EP 13 17 3986.4, completed Aug. 20, 2013 and mailed Aug. 29, 2013; (6 pp).

(56) References Cited

OTHER PUBLICATIONS

Extended European Search Report corresponding to EP 13 17 7437.4, completed Sep. 11, 2013 and mailed Sep. 19, 2013; 6 pages.
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
Extended European Search Report corresponding to EP 13 19 2111.6, completed Feb. 13, 2014 and mailed Feb. 27, 2014; (10 pp).
Extended European Search Report corresponding to EP 13 19 5919.9, completed Feb. 10, 2014 and mailed Mar. 3, 2014; (7 pp).
Extended European Search Report corresponding to EP 08 72 6500.5, completed Feb. 20, 2014 and mailed Mar. 3, 2014; (7 pp).
Extended European Search Report corresponding to EP 13 19 5019.8, completed Mar. 14, 2014 and mailed Mar. 24, 2014; (7 pp).
Extended European Search Report corresponding to EP 13 19 6816.6, completed Mar. 28, 2014 and mailed Apr. 9, 2014; (9 pp).
Extended European Search Report corresponding to EP 13 19 7958.5, completed Apr. 4, 2014 and mailed Apr. 15, 2014; (8 pp).
Extended European Search Report corresponding to EP 13 19 4995.0, completed Jun. 5, 2014 and mailed Jun. 16, 2014; (5 pp.).
Extended European Search Report corresponding to EP 14 15 7195.0, completed Jun. 5, 2014 and mailed Jun. 18, 2014; (9 pp).
Extended European Search Report corresponding to EP 14 15 6342.9, completed Jul. 22, 2014 and mailed Jul. 29, 2014; (8 pp).
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and mailed Sep. 17, 2014; (8 pp).
Extended European Search Report corresponding to EP 14 16 8904.2, completed Sep. 10, 2014 and mailed Sep. 18, 2014; (8 pp).
Extended European Search Report corresponding to EP 13 19 4995.0, completed Jun. 5, 2014 and mailed Oct. 13, 2014; (10 pp).
Extended European Search Report corresponding to EP 13 15 4571.7, completed Oct. 10, 2014 and mailed Oct. 20, 2014; (8 pp).
Extended European Search Report corresponding to EP 14 18 1125.7, completed Oct. 16, 2014 and mailed Oct. 24, 2014; (7 pp).
Extended European Search Report corresponding to EP 14 18 1127.3, completed Oct. 16, 2014 and mailed Nov. 10, 2014; (8 pp).
Extended European Search Report corresponding to EP 14 19 0419.3, completed Mar. 24, 2015 and mailed Mar. 30, 2015; (6 pp).

\* cited by examiner

BUTTRESS SUPPORT DESIGN FOR EEA ANVIL

CROSS-REFERENCE TO RELATED APPLICATIONS

This application is a continuation and claims the benefit of and priority to of U.S. patent application Ser. No. 13/358,544, filed Jan. 26, 2012, now U.S. Pat. No. 9,010,612, the entire disclosure of which is incorporated by reference herein.

BACKGROUND

1. Technical Field

The present disclosure relates to a surgical instrument for applying surgical fasteners or staples to body tissue, and more particularly, to a surgical buttress assembly for use with an end-to-end anastomosis stapling apparatus.

2. Background of Related Art

Anastomosis is a surgical joining of separate hollow organ sections. Typically, an anastomosis procedure follows surgery in which a diseased or defective section of hollow tissue is removed and the remaining end sections are joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Typically, these instruments include an elongated shaft having a handle portion at a proximal end to actuate the instrument and a staple holding component disposed at a distal end. An anvil assembly including an anvil shaft with attached anvil head is mounted to the distal end adjacent the staple holding component. Opposed end sections of the organ to be stapled are clamped between the anvil head and the staple holding component. The clamped tissue is stapled by driving a plurality of staples from the staple holding component so that the ends of the staples pass through the tissue and are deformed by the anvil head.

In use, one end section of the organ is secured about the anvil assembly and the other end section of the organ is held in place adjacent the staple holding component. The shaft of the anvil assembly is removably connected to the instrument. Once the anvil shaft is secured to the instrument, the anvil is drawn into close approximation to the staple holding component. The instrument is then fired to cause the staples to pass through tissue of both sections of the organ and deform against the anvil. During the firing step, a circular knife is advanced to cut tissue inside the staple line, thereby establishing a passage between the two sections of the organ. After firing, the instrument is typically removed by withdrawing the anvil through the staple line, after which the surgeon will carefully inspect the surgical site to ensure a proper anastomosis has been achieved.

While circular staplers are helpful in a number of surgical procedures, problems such as anastomotic leak, tearing of tissue during stapler extraction, bleeding, and other complications may arise. In order to remedy such problems, buttress or reinforcing materials have been utilized. However, due to the inherent difficulty in positioning and securing such materials with the instrument, a need exists for the buttress material that can be safely and effectively positioned with the anvil.

SUMMARY

In accordance with an embodiment of the present disclosure, there is provided an apparatus for joining two hollow organ sections with an annular array of surgical staples. The apparatus includes a staple cartridge component, an anvil component, a buttress member and a buttress mount. The staple cartridge component includes a plurality of surgical staples in an annular array. The anvil component includes an anvil member and a shaft extending therefrom. The anvil member defines a plurality of staple pockets for deforming the surgical staples. The anvil component is movable relative to the staple cartridge component between spaced apart and approximated positions to adjustably clamp tissue between the staple cartridge and anvil components. The buttress member is concentrically aligned with the plurality of staple pockets defined in the anvil member. The buttress mount is detachably secured with the shaft of the anvil component. The buttress mount includes at least one support member radially extending outward to secure the buttress member to the anvil member. The buttress mount at least partially underlying the buttress member to provide support thereto.

In an embodiment, the buttress mount may further include an annular ring member from which the at least one support member radially extends outward. The annular ring member may be configured and dimensioned to receive the shaft of the anvil component therethrough. The at least one support member may be disposed radially inward of the plurality of staple pockets. A radially outer peripheral portion of the at least one support member may be flush with a peripheral edge of the anvil member. The at least one support member may also extend radially outward of at least one of the annular rows of staple pockets. Alternatively, the at least one support member may at least partially overlie at least one of the annular rows of staple pockets.

The at least one support member may have a radially varying thickness. The buttress member may have an annular configuration. In particular, the buttress member may be disposed in a juxtaposed relation with the plurality of staple pockets. The buttress mount may engage a proximal surface of the buttress member. Alternatively, the buttress mount may engage a distal surface of the buttress member. The buttress member may be made of a biodegradable material. The anvil member may define a recess configured and dimensioned to receive the buttress mount therein to provide securement of the buttress mount therein. The at least one support member of the buttress mount may engage an inner wall of the recess to provide securement of the buttress mount thereagainst. The buttress member and the buttress mount may be monolithically formed as a single construct. In addition, the apparatus may further include a knife member concentrically arranged with the plurality of surgical staples in the staple cartridge component. The knife member may be movable relative to the staple cartridge component. In particular, the at least one support member of the buttress mount may be disposed radially inward of the knife member when the knife member engages the buttress member.

In accordance with another embodiment of the present disclosure, there is provided an apparatus for joining two hollow organ sections with an annular array of surgical staples. The apparatus includes a staple cartridge component, an anvil component, a knife member, a buttress member, and a buttress mount. The staple cartridge component includes a plurality of surgical staples in an annular array. The anvil component defines a plurality of staple pockets for deforming the surgical staples. The anvil component is movable relative to the staple cartridge component between spaced apart and approximated positions to adjustably clamp tissue between the staple cartridge and anvil components. The knife member is concentrically arranged with the plurality of surgical staples in the staple cartridge component. The knife member is movable relative to the staple cartridge component. The buttress member is concentrically aligned with the anvil component. The buttress mount is detachably secured with the anvil component. The buttress mount includes a core ring, an outer ring, and at least one spoke extending between and interconnecting the core ring and the outer ring. The buttress mount is configured and adapted to secure the buttress member with the anvil member. The buttress mount at least partially underlying the buttress member to provide support thereto.

In an embodiment, the buttress member may be concentrically aligned with the plurality of staple pockets. The outer ring may at least partially overlap the plurality of staple pockets in the annular array. The buttress mount may engage a proximal surface of the buttress member. The buttress mount may engage a distal surface of the buttress member. The outer ring may be disposed radially inward of the knife member when the knife member is actuated to engage the buttress member.

In accordance with still another embodiment of the present disclosure, there is provided an apparatus for joining two hollow organ sections with an annular array of surgical staples. The apparatus includes a handle assembly, an elongate tubular member, a staple cartridge component, an anvil component, a knife member, a buttress member, and a buttress mount. The handle assembly includes a firing trigger. The elongate tubular member extends distally from the handle assembly. The staple cartridge component is coupled to a distal portion of the elongate tubular member. The staple cartridge component includes a plurality of surgical staples in an annular array. The anvil component defines a plurality of staple pockets for deforming the surgical staples. The anvil component is movable relative to the staple cartridge component between spaced apart and approximated positions to clamp tissue between the staple cartridge and anvil components. The knife member is concentrically arranged with the plurality of surgical staples in the staple cartridge component. The knife member is movable relative to the staple cartridge component. The buttress member is concentrically aligned with the anvil component. The buttress mount is detachably secured with the anvil component. The buttress mount includes at least one support member radially extending outward, from a shaft of the anvil component when the buttress mount is mounted on the anvil component to secure the buttress member to the anvil component. The buttress mount at least partially underlies the buttress member to provide support thereto.

In an embodiment, the buttress mount may further include an annular ring member from which the at least one support member radially extends outward. The at least one support member may be disposed radially inward of the plurality of staple pockets. A peripheral portion of the at least one support member may be flush with a peripheral edge of the anvil member. The at least one support member may extend radially outward of at least one of the annular rows of staple pockets. The at least one support member may at least partially overlie at least one of the annular rows of staple pockets.

BRIEF DESCRIPTION OF THE DRAWINGS

Various embodiments of the present disclosure are described hereinbelow with reference to the drawings, wherein.

DETAILED DESCRIPTION OF EMBODIMENTS

Figure 1:
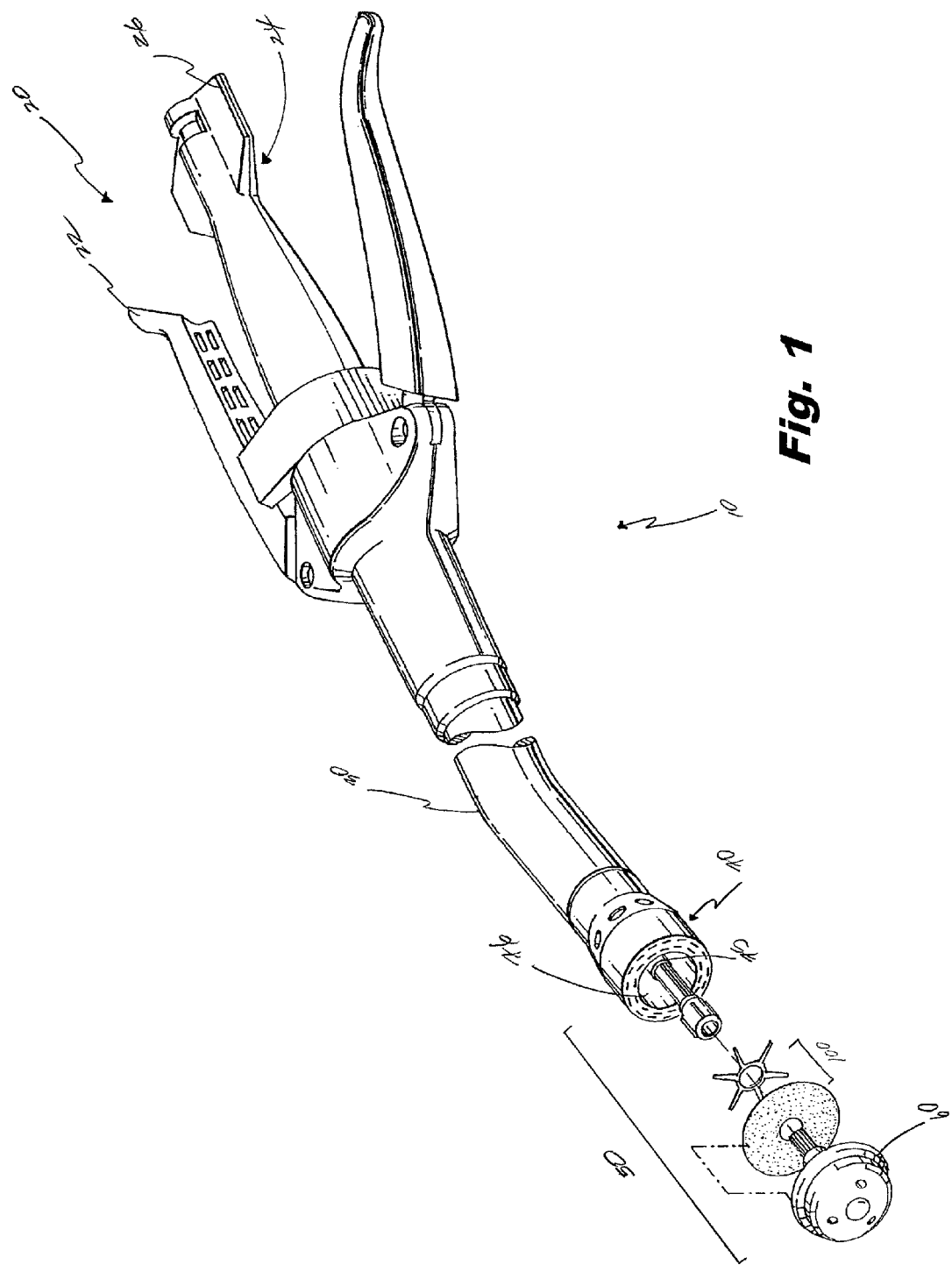
FIG. 1 is a perspective view of an annular surgical stapling apparatus configured for use with a surgical buttress assembly in accordance with an embodiment of the present disclosure, illustrating an anvil assembly and the buttress assembly detached from the surgical stapling apparatus.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

With reference to FIG. 1, a surgical stapling apparatus 10 for performing circular anastomosis of hollow organs is shown. Surgical stapling apparatus 10 drives a circular array of staples 7 (FIG. 15) through the end sections of each organ and simultaneously fires an annular knife 76 (FIG. 15) to sever any tissue interior of the driven circular array of staples 7 to free the tubular passage, and thereby joining two ends of the organ. Surgical stapling apparatus 10 includes a handle assembly 20 having a pair of pivotable actuating handle members 22 and an advancing means 24 including a rotatable grip member 26, an elongate body portion 30 extending distally from handle assembly 20, and a head portion 50 including an anvil assembly 60, a staple cartridge assembly 70, and a surgical buttress assembly 100 in accordance with an embodiment of the present disclosure. The components of surgical apparatus 10 are generally formed from thermoplastics including polycarbonates, and metals including stainless steel and aluminum. The particular material selected to form a particular component will depend upon the strength requirements of the particular component. Staples 7 are of a conventional type and include a backspan having a pair of legs extending from the backspan. The legs terminate in tissue penetrating tips.

Figure 14:
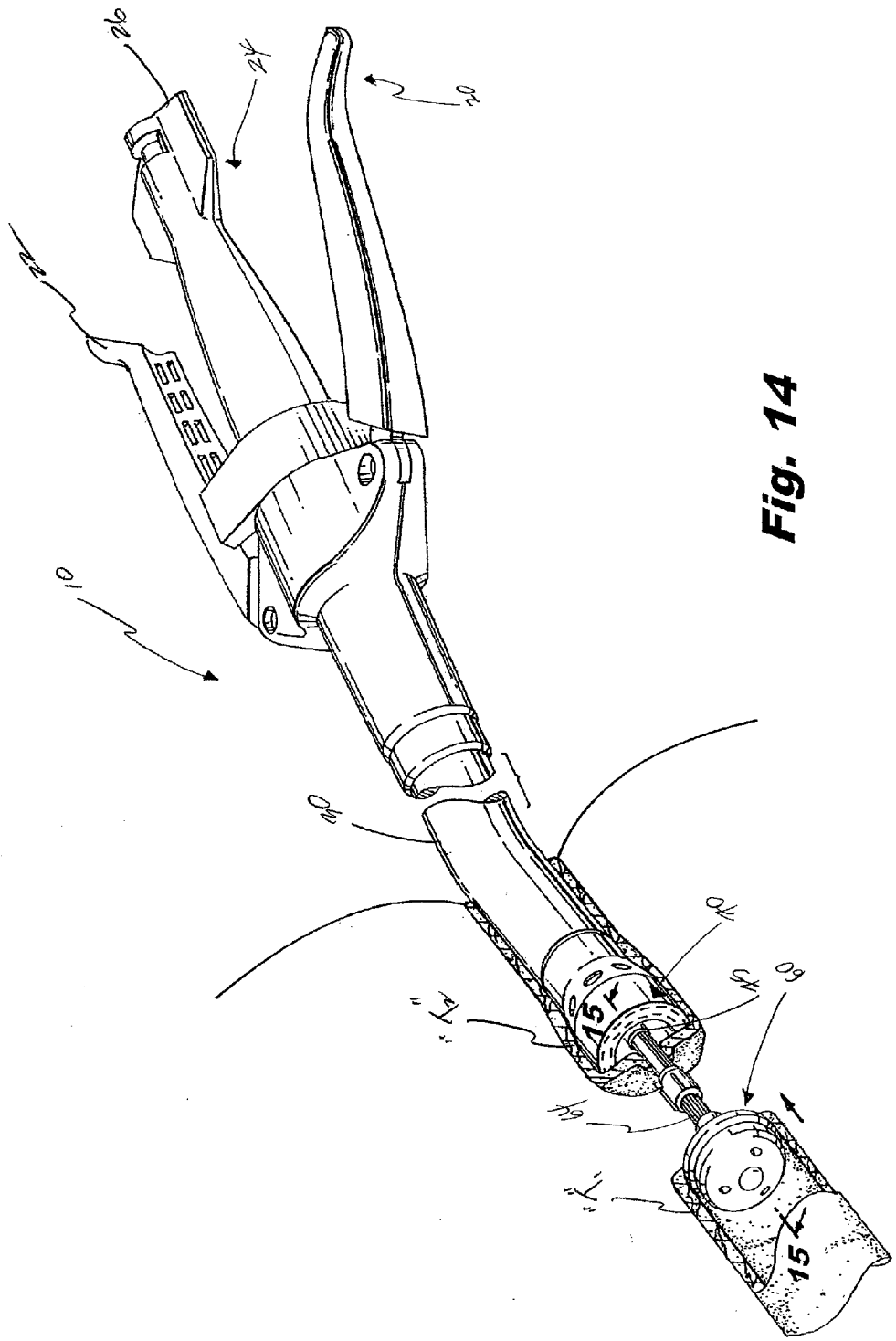
FIG. 14 is a perspective view of the annular surgical apparatus of FIG. 1, illustrating insertion of the apparatus through two hollow organ sections.

Handle assembly 20 can be actuated to approximate anvil assembly 60 relative to staple cartridge assembly 70 and to apply a pair of annular arrays of staples 7 through tissue. In order to properly position tissue in head portion 50, rotatable grip member 26 may be rotated to move anvil assembly 60 axially relative to staple cartridge assembly 70 between a spaced apart position and an approximated position in which anvil assembly 60 is positioned adjacent staple cartridge assembly 70 to clamp tissue therebetween. Handle members 22 may be squeezed to fire staples 7 through tissue to join two segments "$T_1$," "$T_2$" (FIG. 14) of tubular tissues together, as will be discussed in detail below.

Elongate body portion 30 is constructed to have a slightly curved/bent shape along its length. However, elongate body portion 30 may also be straight, as well as flexible to bend to any configuration. The length, shape and/or the diameter of elongate body portion 30 may be varied to suit a particular surgical procedure.

With reference to FIGS. 1-4, head portion 50 includes, a staple cartridge assembly 70, an anvil assembly 60 and a surgical buttress assembly 100 detachably secured with anvil assembly 60. Staple cartridge assembly 70 may be fixedly connected to a distal end portion of elongate body portion 30 or may be configured to concentrically fit within the distal end portion of elongate body portion 30. In particular, staple cartridge assembly 70 defines a pair of annular arrays of staple receiving slots 72 (FIG. 15) having a staple 7 disposed in each one of staple receiving slots 72. In addition, staple cartridge assembly 70 includes a cylindrical knife 76 concentrically arranged with the pair of annular array of staples 7 and a plurality of staple pushers 9 (FIG. 15) each disposed in staple receiving slot 72 to eject staple 7 through slot 72. Staples 7 travel through slots 72 and tissue toward anvil assembly 60.

Figure 15:
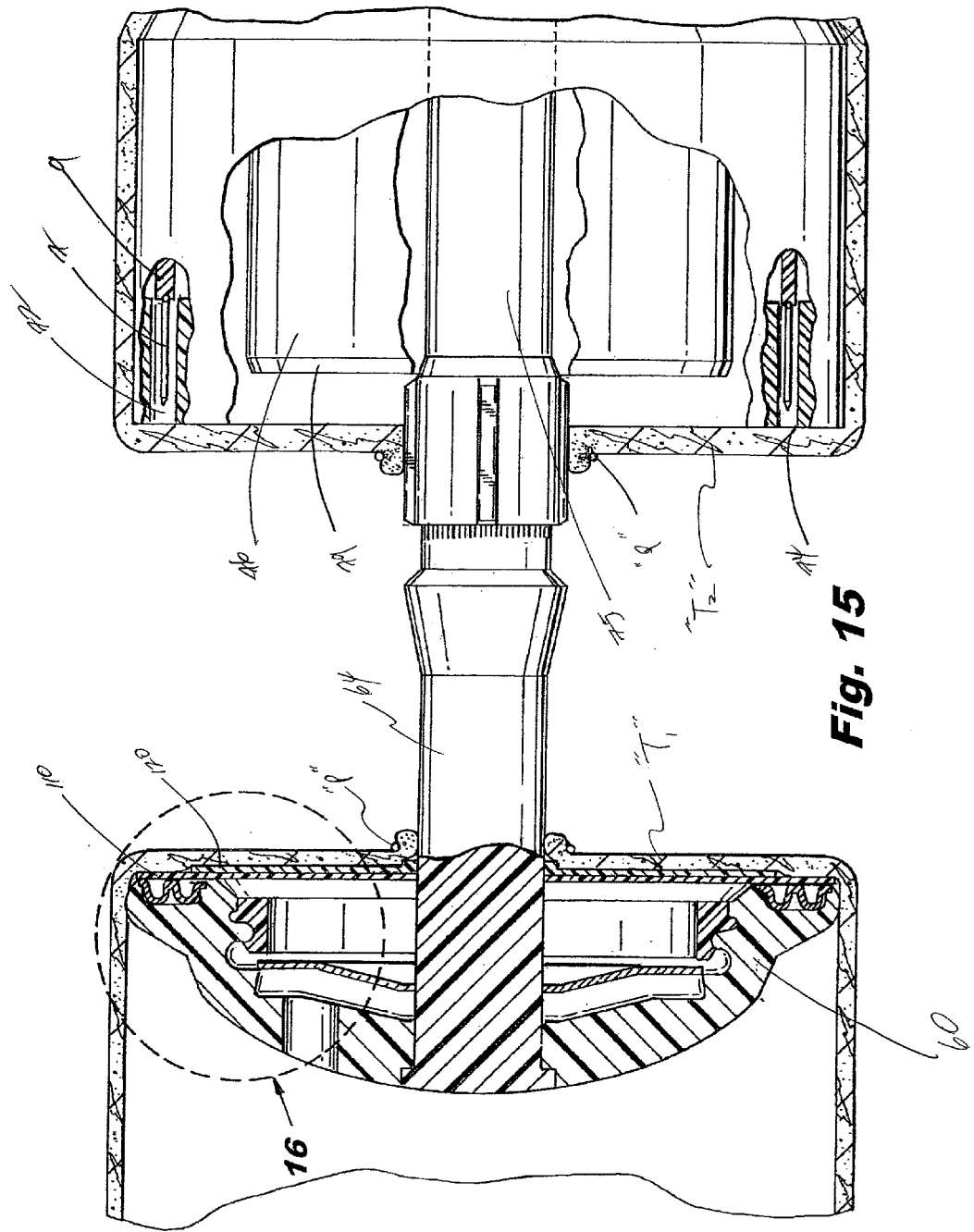
FIG. 15 is an enlarged, partial longitudinal cross-sectional view of a head portion of the apparatus of FIG. 14.
Figure 16:
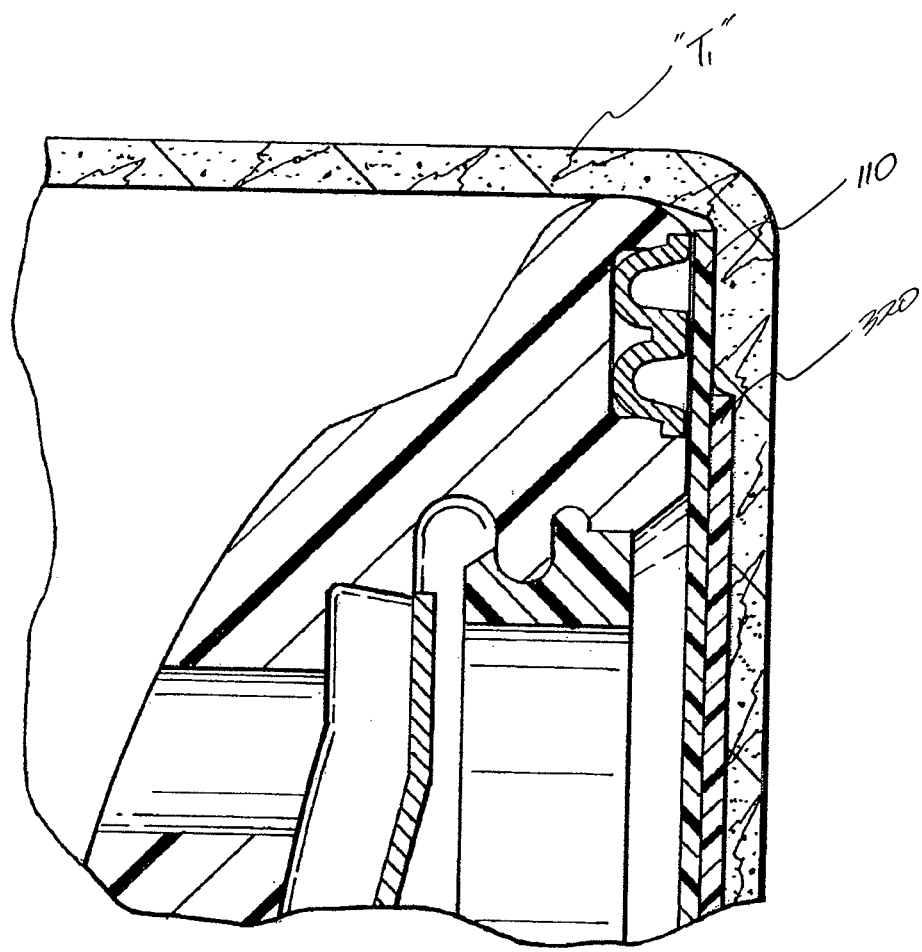
FIG. 16 is an enlarged view of the area of detail indicated in FIG. 15.

With brief reference to FIG. 15, cylindrical knife 76 includes a distal rim 79 defining a knife blade adapted to cut tissue and portions of surgical buttress assembly 100. Upon actuation of handle members 22, cylindrical knife 76 is moved distally to cut tissue and portions of surgical buttress assembly 100, and the plurality of pushers 9 are moved distally to eject staples 7 from the staple receiving slots 72 toward anvil assembly 60.

Figure 2:
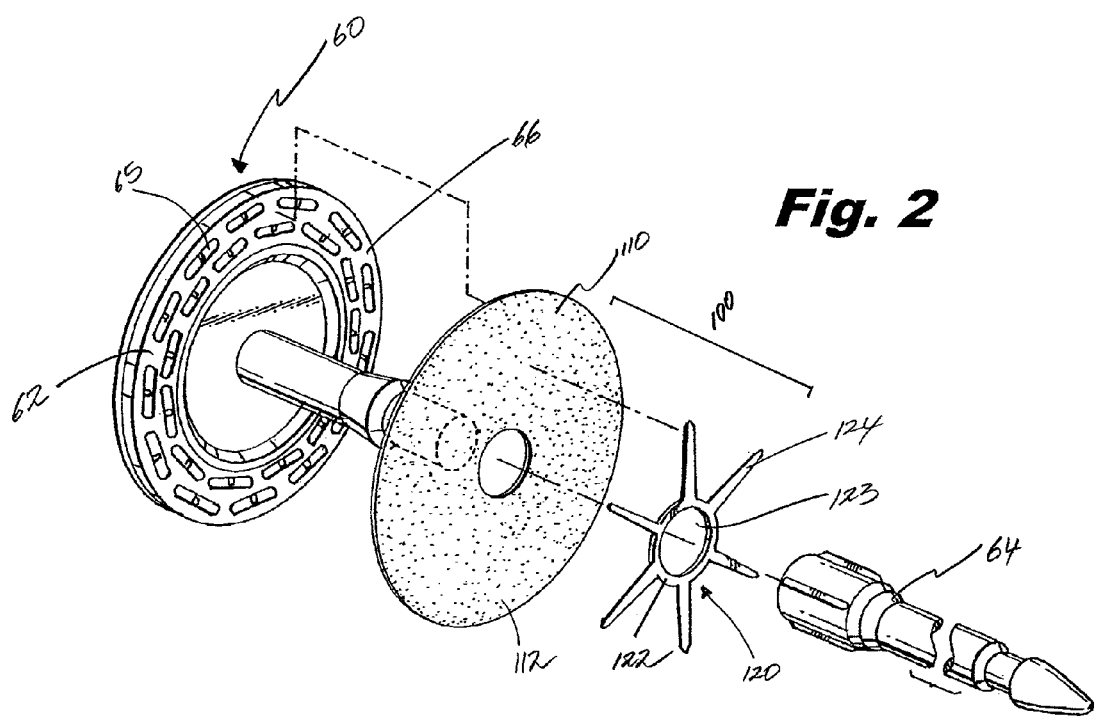
FIG. 2 is an exploded perspective view of the anvil assembly and the buttress assembly of the surgical stapling apparatus of FIG. 1 with parts separated.

With particular reference back to FIG. 2, positioned distally of staple cartridge assembly 70 is anvil assembly 60 including an anvil member 62 and a shaft 64 extending proximally from anvil member 62. Anvil member 62 includes a plurality of staple pockets 65 for receiving and deforming staples 7. Shaft 64 is configured to be detachably received in approximation shaft 75 (FIG. 1) disposed in elongate body portion 30. Approximation shaft 75 is operatively coupled with rotatable grip member 26 of handle assembly 20, whereby rotation of rotatable grip member 26 moves approximation shaft 75 axially. Such axial movement of approximation shaft 75 is imparted to anvil assembly 60. In this manner, anvil assembly 60 is movable axially relative to staple cartridge assembly 70 between a spaced apart position and an approximated position in which anvil assembly 60 is positioned adjacent staple cartridge assembly 70 to adjustably clamp tissue between anvil assembly 60 and staple cartridge assembly 70.

Examples of instruments for performing circular anastomosis of hollow organs are described in U.S. Pat. Nos. 6,053,390, 5,588,579, 5,119,983, 5,005,749, 4,646,745, 4,576,167, and 4,473,077, each of which is hereby incorporated herein in its entirety by reference.

Figure 3:
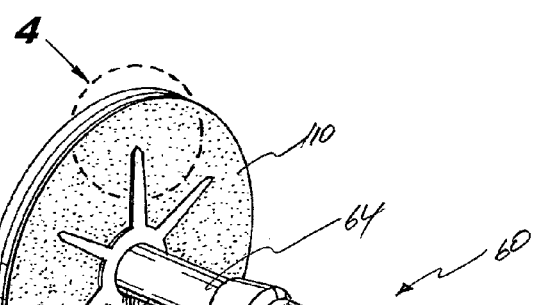
FIG. 3 is a perspective view of the anvil assembly of FIG. 2 having the buttress assembly of FIG. 2 mounted thereon.
Figure 4:
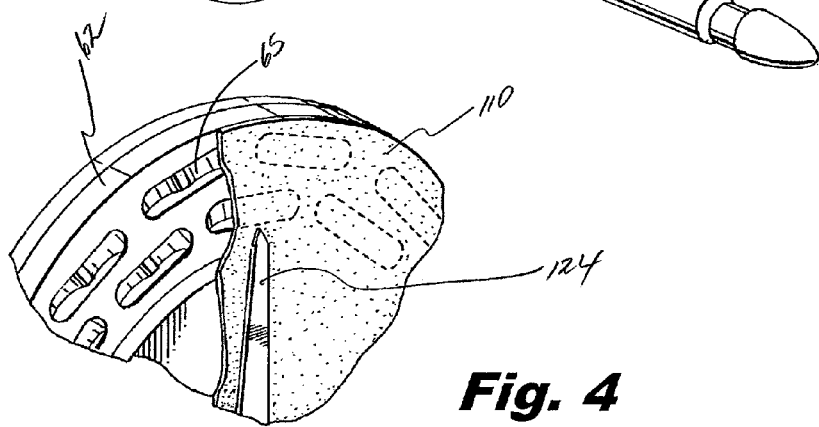
FIG. 4 is a cutaway perspective view of the area of detail indicated in FIG. 3.

With continued reference to FIGS. 2-4, a buttress member 110 and a buttress mount 120 are concentrically arranged with one another. Buttress member 110 is provided to reinforce and seal staple lines applied to tissue by surgical stapling apparatus 10.

Buttress member 110 is fabricated from a biocompatible material which is bioabsorbable or non-absorbable, and can also be made from natural or synthetic materials. It should be understood that any combination of natural, synthetic, bioabsorbable, and non-bioabsorbable materials may be used to form buttress member 110.

In addition, buttress member 110 may be porous, non-porous, or combinations thereof. It is also envisioned that buttress member 110 described herein may contain a plurality of layers in which any combination of non-porous and porous layers may be configured. For example, buttress member 110 may be formed to include multiple non-porous layers and porous layers that are stacked in an alternating manner. In another example, buttress member 110 may be formed in a "sandwich-like" manner wherein the outer layers of buttress member 110 include porous layers and the inner layers are non-porous layers. Examples of multi-layered buttress members are disclosed in U.S. Patent Application Publication No. 2009/0001122, filed on Jun. 27, 2007, entitled "Buttress and Surgical Stapling Apparatus," the entire disclosure of which is hereby incorporated by reference therein.

In particular, the use of non-porous layers in buttress member 110 may enhance the ability of buttress member 110 to resist tears and perforations during the manufacturing, shipping, handling, and stapling processes. In addition, the use of a non-porous layer in the surgical buttress may also retard or inhibit tissue ingrowth from surrounding tissues, and thereby act as an adhesion barrier and/or inhibit the formation of unwanted scar tissue.

In addition, at least one bioactive agent may be combined with buttress member 110. The agent may be disposed on a surface of the surgical buttress and/or impregnated therein. In these embodiments, buttress member 110 can also serve as a vehicle for delivery of the bioactive agent. The term "bioactive agent," as used herein, is used in its broadest sense and includes any substance or mixture of substances that have clinical use.

With continued reference to FIGS. 2-4, buttress member 110 has an annular profile configured to be concentrically aligned with anvil assembly 60. In particular, buttress member 110 is mounted on a proximal surface 66 of anvil assembly 60, and buttress mount 120 is disposed proximal of buttress member 110. The annular profile of buttress member 110 is configured and dimensioned to at least be flush with an outer peripheral edge of anvil member 62 when mounted on anvil assembly 60.

Buttress mount 120 includes a core ring 122 and support arms 124 radially extending outward from core ring 122. Support arms 124 are circumferentially arranged about core ring 122 and are configured and dimensioned to be affixed to a proximal surface 112 of buttress member 110 by, for example, over molding, ultrasonic welding, melt pressing or melt pressing in conjunction with other polymers or with adhesives. Core ring 122 includes a hole 123 configured and dimensioned to receive shaft 64 of anvil assembly 60 therethrough when being mounted to anvil assembly 60. In particular, hole 123 is configured and dimensioned to provide a tight or friction fit against shaft 64 to enable securement of buttress member 110 between anvil member 62 and buttress mount 120. It is contemplated that core ring 122 may be configured as a split ring (i.e., including a break along a length thereof) to accommodate various diameter shafts.

Other shapes for the buttress support are contemplated, and the buttress support may incorporate straight or curved members having a variety of cross-sectional shapes.

With particular reference now to FIG. 4, buttress member 110 is in a superposed relation with the pair of annular arrays of staple pockets 65 defined in anvil member 62. In particular, radially extending support arms 124 of buttress mount 120 are configured and sized to terminate radially inward of the pair of annular arrays of staple pockets 65, such that when staples 7 are ejected through the pair of annular arrays of staple receiving slots 72, the legs of each staple 7 penetrate through tissue and buttress member 110 into staple pockets 65. Under such a configuration, support arms 124 of buttress mount 120 are not affected by the staple formation and, likewise, the support arms do not affect the staple formation. In this manner, upon actuation of handle members 22, a portion of buttress member 110 is stapled with tissue to reinforce tissue, and the remaining portions of buttress member 110 and buttress mount 120 are cut and detached from the portion of buttress member 110 stapled with tissue. However, it is also contemplated that support arm 124 may be configured and sized to terminate radially inward of cylindrical knife 76 when cylindrical knife 76 is actuated to cut tissue and buttress mount 120. In this manner, severing of support arm 124 by cylindrical knife 76 may be eliminated.

Figure 5:
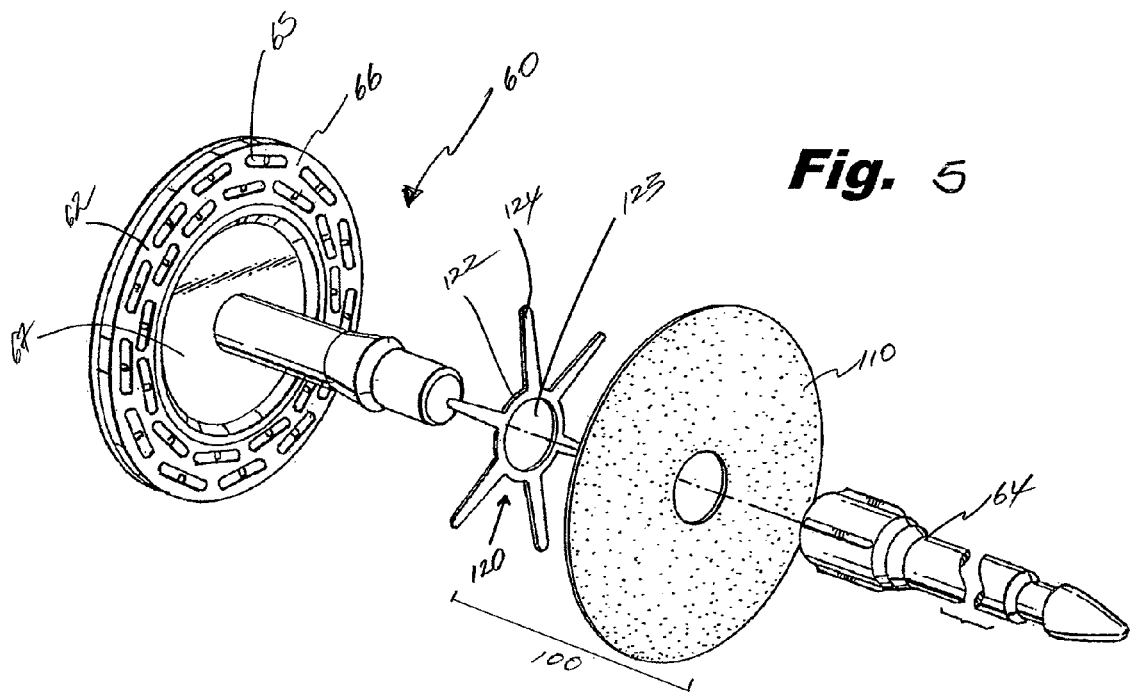
FIG. 5 is an exploded perspective view of the anvil assembly and the buttress assembly of FIG. 2 with parts separated, illustrating invertible use of the buttress assembly.
Figure 6:
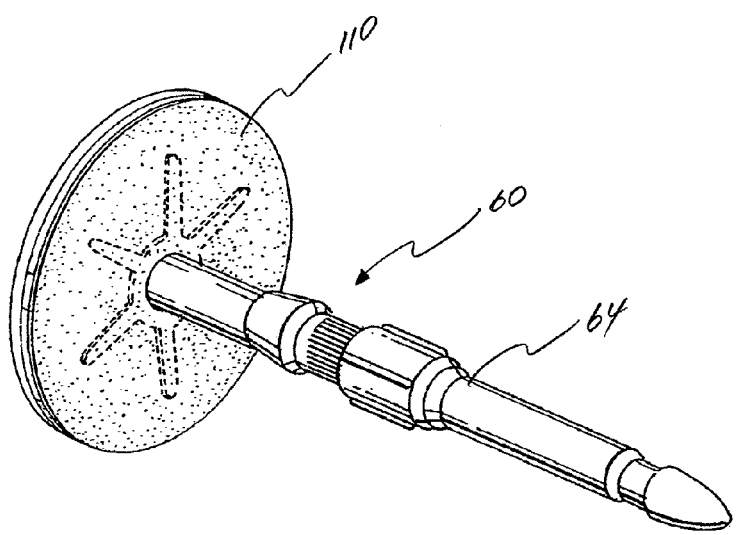
FIG. 6 is a perspective view of the anvil assembly of FIG. 5 having the buttress assembly of FIG. 5 mounted thereon.

With reference now to FIGS. 5 and 6, it is also envisioned that buttress assembly 100 may be used in an inverted position. Specifically, buttress mount 120 is secured with buttress member 110, by any of the methods described hereinabove, so that the buttress mount 120 is arranged distal of buttress member 110. Furthermore, buttress mount 120 may be configured and dimensioned to be received in a recess 67 defined in anvil member 62. Additionally or alternatively, a hole 123 defined by core ring 122 provides a tight fit against shaft 64 of anvil assembly 60. Moreover, support arms 124 are configured and dimensioned to provide a tight fit with a peripheral edge of recess 67, which further improves the securement of buttress member 110 with anvil assembly 60.

The distal arrangement of buttress mount 120 with respect to buttress member 110 can provide a flat surface contact between buttress member 110 and the proximal surface 66 of anvil member 62, to thereby further enhance staple formation through tissue.

Figure 7:
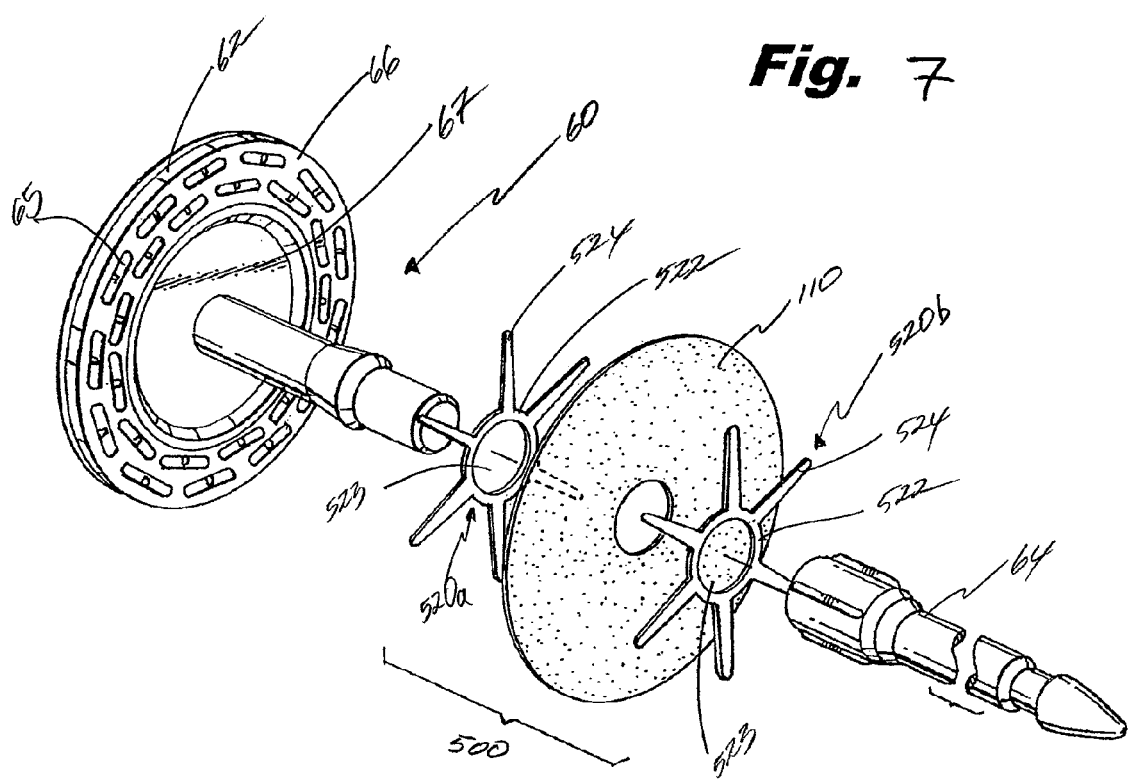
FIG. 7 is an exploded perspective view of the anvil assembly of FIG. 1 and a buttress assembly in accordance with another embodiment of the present disclosure, with parts separated.

With reference now to FIG. 7, it is also envisioned that buttress member 110 may be supported by a pair of buttress mounts 520a, 520b. In particular, buttress mount 520a is arranged distal of buttress member 110, and buttress mount 520b is arranged proximal of buttress member 110. Buttress mounts 520a, 520b are attached to buttress member 110 by any of the methods described hereinabove. Buttress mounts 520a, 520b are substantially identical to buttress mount 120 described hereinabove, and thus will not be described herein in the interest of brevity. Buttress mounts 520a, 520b are substantially identical and as such, buttress assembly 500 may be used interchangeably. Holes 523 of respective buttress mounts 520a, 520b are configured and dimensioned to receive shaft 64 of anvil assembly 60 therethrough to provide a tight or friction fit therewith. In addition, buttress mount 520a include support arms 524 radially extending outward from core ring 522 to provide a tight fit around the peripheral edge of recess 67 of anvil assembly 60 to further improve securement of buttress member 110 with anvil assembly 60. The entire assembly may be inverted, and buttress mount 520b may also include support arms 524 configured and dimensioned to provide a tight fit against the peripheral edge of recess 67 of anvil assembly 60. While support arms 524 of buttress mount 520a are shown to be in radial registration with support arms 524 of buttress mount 520b, it is contemplated that support arms 524 of buttress mounts 520a, 520b may be out of radial registration with one another. The buttress mounts 520a and 520b may have different configurations including arms that are curved or straight, having a variety of cross-sectional shapes. The configuration of buttress mount 520a may be different from the configuration of buttress mount 520b.

Figure 8:
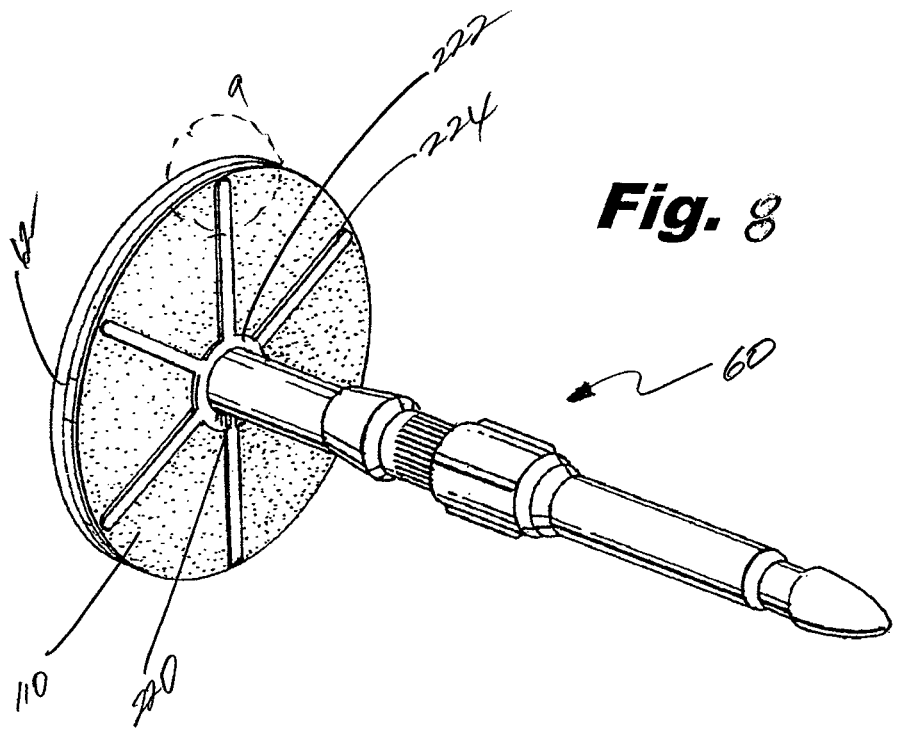
FIG. 8 is a perspective view of the anvil assembly of FIG. 1 having a buttress assembly in accordance with another embodiment of the present disclosure mounted thereon.
Figure 9:
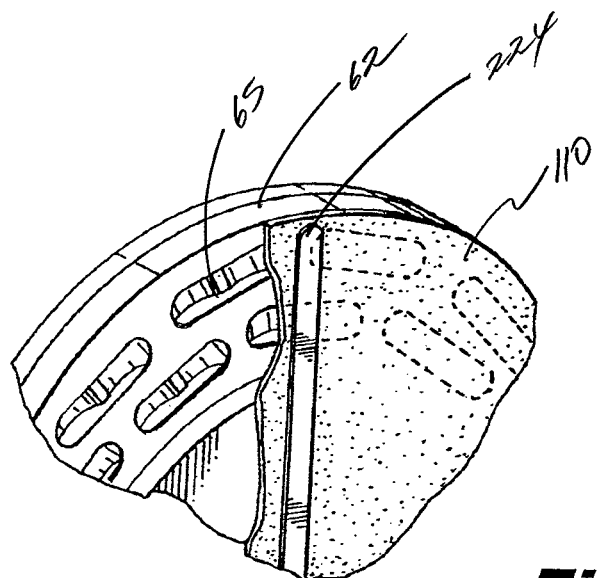
FIG. 9 is a cutaway perspective view of the area of detail indicated in FIG. 8.

With reference to FIGS. 8 and 9, it is further contemplated that a buttress mount 220 may include support arms 224 that radially extend outward from a core ring 222 and that are substantially flush with an outer peripheral edge of anvil member 62 when mounted on anvil assembly 60. Under such a configuration, a portion of each support arm 224 is stapled to tissue to reinforce tissue, and the remaining portions (i.e., portions radially inward of cylindrical knife 76) of buttress member 110 and buttress mount 120 are cut and detached from the portion of buttress member 110 that is stapled to tissue.

By providing a greater area of contact between buttress member 110 and support arms 224, the force applied to buttress member 110 by support arms 224 is more evenly distributed throughout buttress member 110, which may inhibit tearing or damage to buttress member 110. Under such a configuration, it is further contemplated that support arms 224 may have varying thickness. In particular, a portion of support arm 224 that is stapled to tissue may have a minimal thickness, e.g., a thickness substantially smaller than the thickness of a portion of support arm 224 adjacent core ring 222, such that any effect of the thickness of support arms 224 on staple formation is minimized. In addition, it is further envisioned that the portion of support arms 224 that are stapled with buttress member 110 may be formed of bioabsorbable and/or biodegradable material.

Figure 10:
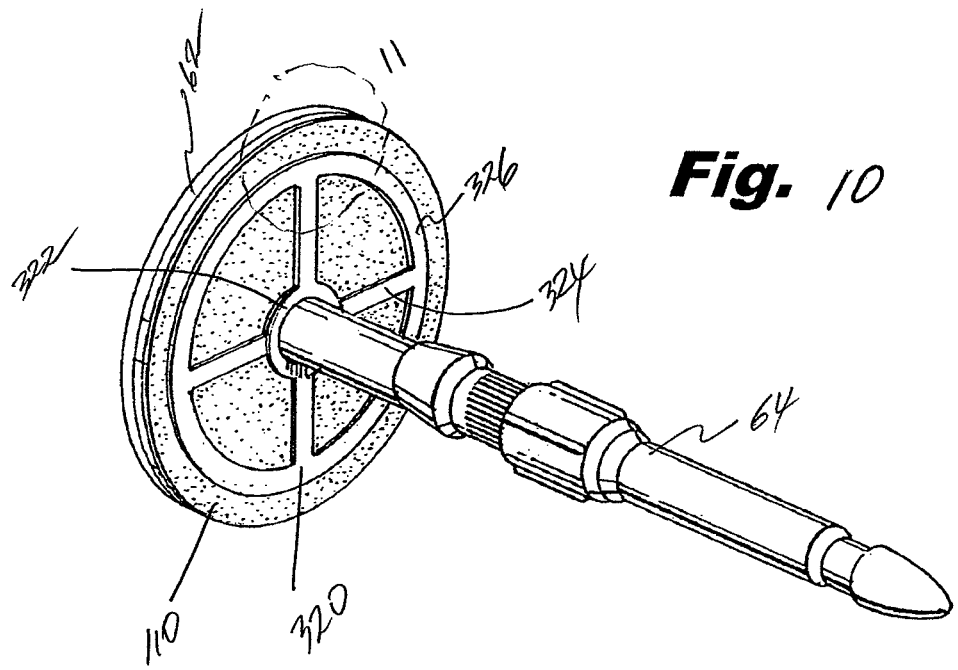
FIG. 10 is a perspective view of the anvil assembly of FIG. 1 having a buttress assembly in accordance with another embodiment of the present disclosure mounted thereon.
Figure 11:
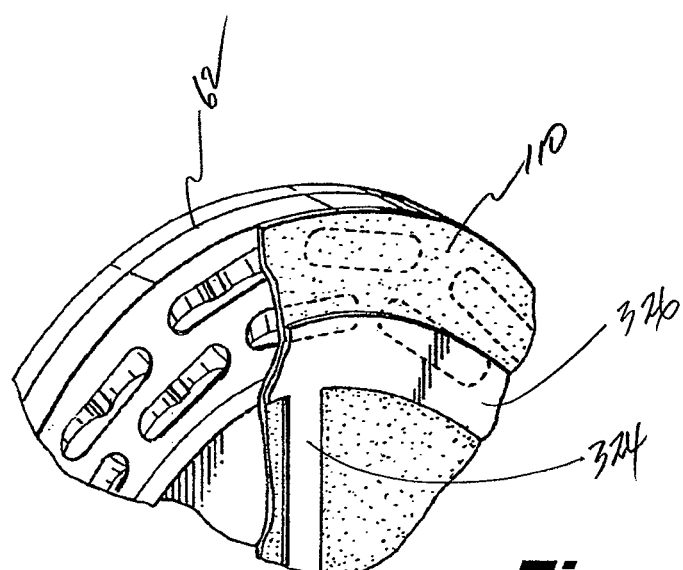
FIG. 11 is a cutaway perspective view of the area of detail indicated in FIG. 10.

With reference to FIGS. 10 and 11, a buttress mount 320 in accordance with another embodiment of the present disclosure is illustrated. Buttress mount 320 includes a core ring 322 configured and dimensioned to receive shaft 64 of anvil assembly 60 therethrough, an outer ring 326 concentrically arranged with core ring 322 and spokes 324 radially extending outward from core ring 322 to outer ring 326, thereby interconnecting core ring 322 and outer ring 326. Outer ring 326 provides additional support for buttress member 110 against anvil member 62. In particular, outer ring 326 may greatly reduce the potential for buttress member 110 to fold over, dislodge or separate from anvil assembly 60. In particular, the force applied to buttress member 110 by buttress mount 320 is more evenly distributed throughout buttress member 110, which may inhibit tear or damage to buttress member 110.

With particular reference to FIG. 11, outer ring 326 is at least partially disposed in the staple formation portion of buttress member 110, whereby only a portion of outer ring 326 is stapled to buttress member 110 and tissue, and the remaining portions of outer ring 326 are cut and detached from the portion of buttress member 110 stapled to tissue. As discussed hereinabove with respect to support arm 224, outer ring 326 may have a minimal thickness at a peripheral portion thereof to minimize interference with staple formation. Additionally, outer ring 326 and/or buttress mount 320, as a whole, may be made of biodegradable and/or bioabsorbable material, such that the portion of outer ring 326 that is stapled to buttress member 110 and tissue is degraded over time. Alternatively, the outer ring 326 can be positioned inwardly of the staple line, or inwardly of the cut line.

Figure 12:
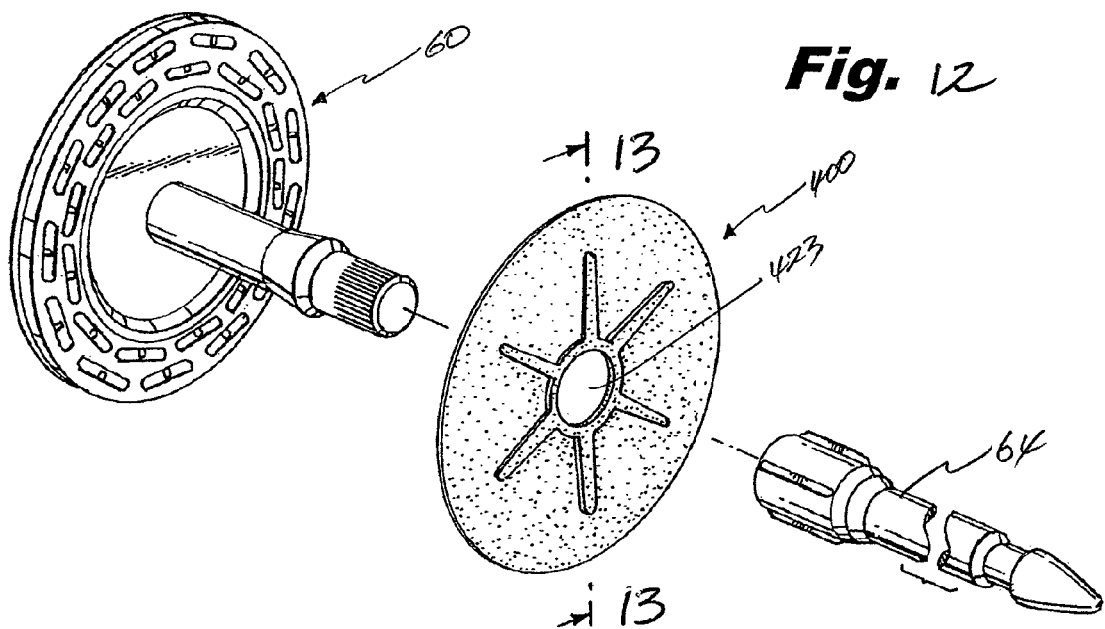
FIG. 12 is an exploded perspective view of the anvil assembly of FIG. 1 and a buttress assembly in accordance with another embodiment of the present disclosure with parts separated.
Figure 13:
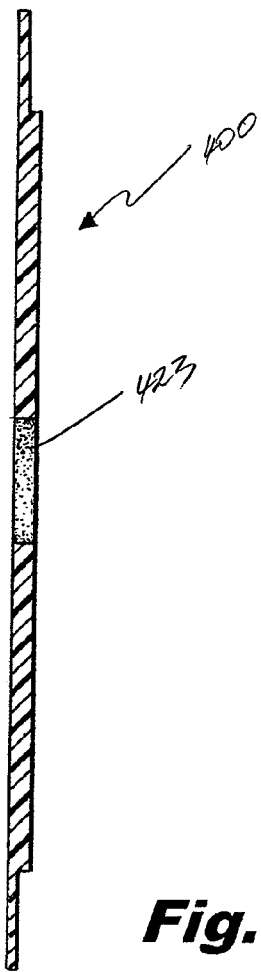
FIG. 13 is a side cross-sectional view of a buttress assembly of FIG. 12 taken along section line 13-13 in FIG. 12.

With reference to FIGS. 12 and 13, while buttress mounts 120, 220, 320 and buttress member 110 have been described hereinabove as separate components that are attached to each other by the methods describe hereinabove, it is also envisioned that buttress member and buttress support may be monolithically formed as a single construct. Monolithically formed buttress assembly 400 defines a common through hole 423 configured and dimensioned to receive shaft 64 of anvil assembly 60 therethrough to provide a tight fit therewith. Alternatively, the buttress member and buttress support can be formed from different materials that are bonded or otherwise attached to one another.

With reference now to FIGS. 14-17, surgical stapling apparatus 10 is used in an anastomosis procedure to effect joining of, for example, two opposing intestinal sections "$T_1$," "$T_2$." The anastomosis procedure is typically performed using minimally invasive surgical techniques including laparoscopic means and instrumentation. Initially, a diseased intestinal section is removed. Thereafter, anvil assembly 60 is inserted to the operative site either through a surgical incision or transanally and is positioned within the intestinal section "$T_1$." Elongate body portion 30 of surgical stapling apparatus 10 including staple cartridge assembly 70 is inserted transanally into the other intestinal section "$T_2$." Intestinal sections "$T_1$," "$T_2$" are then temporarily secured about their respective components (e.g., shaft 64 of anvil assembly 60 and the distal end of elongate body portion 30) by conventional means such as a purse string suture "P."

Figure 17:
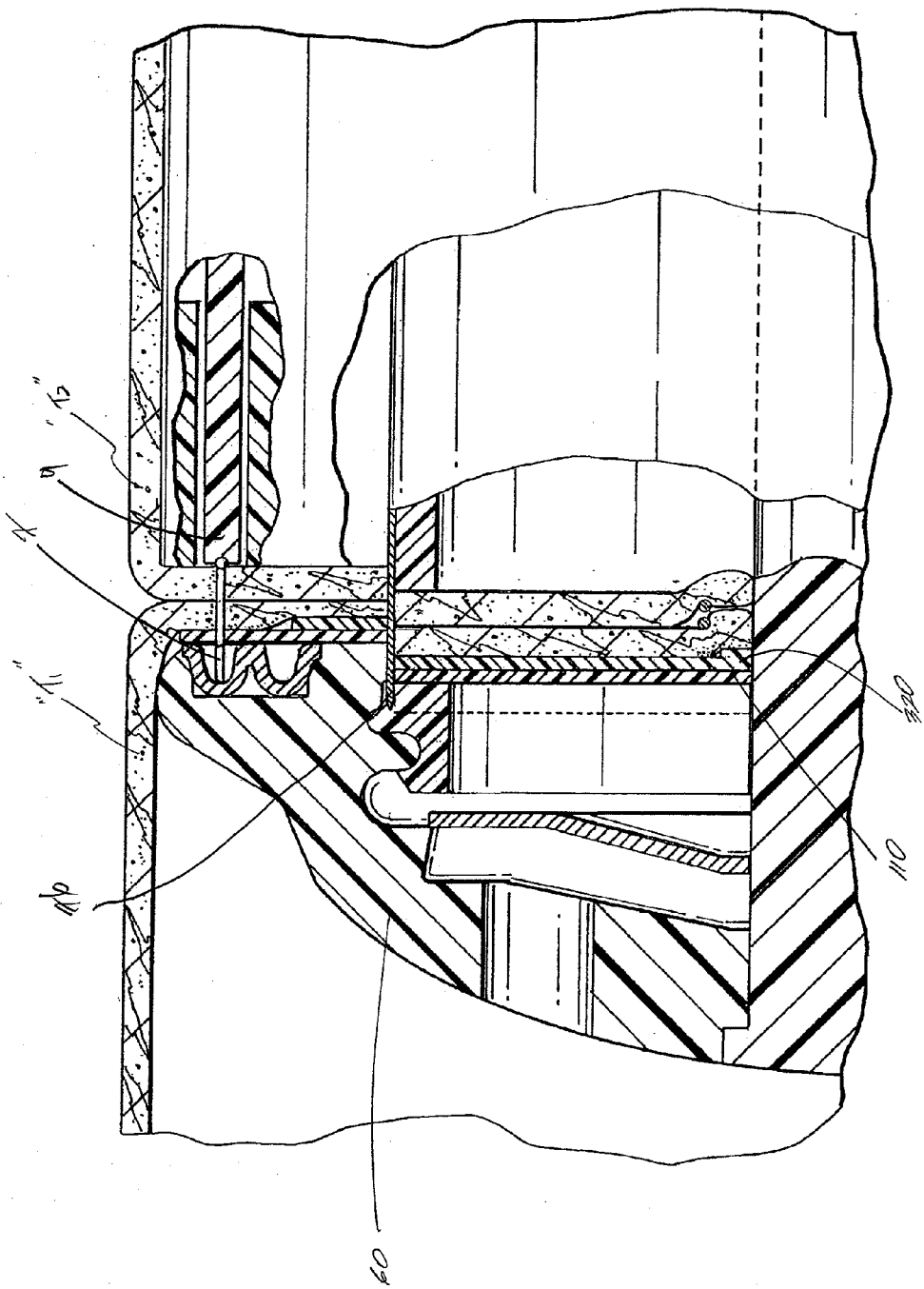
FIG. 17 is an enlarged, partial longitudinal cross-sectional view of the head portion of the apparatus of FIG. 15, illustrating stapling and cutting of the two hollow organ sections.

Thereafter, the clinician maneuvers anvil assembly 60 until the proximal end of shaft 64 is inserted into the distal end of approximation shaft 75 disposed in elongate body portion 30 of surgical stapling apparatus 10. Shaft 64 engages approximation shaft 75 to be operable as a unitary construct, as shown in FIG. 15. Anvil assembly 60 and elongate body portion 30 are then approximated to approximate intestinal sections "$T_1$," "$T_2$," as shown in FIG. 17. Surgical stapling apparatus 10 is then fired, effecting stapling of intestinal sections "$T_1$," "$T_2$" to one another, while cylindrical knife 76 cuts a portion of buttress member 110 and tissue disposed radially inward of cylindrical knife 76, and thereby detaching buttress mount 320 and an inner portion of buttress member 110 from the portion of buttress member 110 that is clamped (approximated) between distal surface 74 of staple cartridge assembly 70 and proximal surface 66 of anvil assembly 60 to complete the anastomosis.

In a further embodiment, a buttress member can be superposed in relation with the annular rows of staple slots defined in the staple cartridge assembly 70. In a particular example, radially extending support arms of buttress mount are attached to a core ring and are configured and sized to terminate radially inward of the pair of annular rows of staple slots 72 (see FIG. 15), such that when staples 7 are ejected through the pair of annular arrays of staple receiving slots 72, the legs of each staple 7 penetrate through tissue and buttress member into staple pockets 65. Alternatively, the support arms can terminate adjacent the rows of staple slots 72. Upon actuation of handle members 22, a portion of buttress member is stapled with tissue to reinforce tissue, and the remaining portions of buttress member and/or buttress mount are cut and detached from the portion of buttress member stapled with tissue. The support arms can be configured to engage the inner surface of a recess in the staple cartridge assembly. Additionally or alternatively, the core ring of the buttress support frictionally engages the shaft. In addition, in certain embodiments, a pair of buttress supports can be used to mount the buttress member on the staple cartridge, as discussed above.

Although the illustrative embodiments of the present disclosure have been described herein with reference to the accompanying drawings, the above description, disclosure, and figures should not be construed as limiting, but merely as exemplifications of particular embodiments. For example, buttress member and buttress support may be secured with approximation shaft 75 disposed in staple cartridge assembly 70, whereby buttress assembly 100 is in a superposed relation with a tissue contacting surface of staple cartridge assembly 70. It is to be understood, therefore, that the disclosure is not limited to those precise embodiments, and that various other changes and modifications may be effected therein by one skilled in the art without departing from the scope or spirit of the disclosure.

What is claimed is:

1. An apparatus for joining two hollow organ sections with an annular array of surgical staples, the apparatus comprising:
   a staple cartridge component including a plurality of surgical staples in an annular array;
   an anvil component including an anvil member and a shaft extending therefrom, the anvil member defining a plurality of staple pockets for deforming the plurality of surgical staples, the anvil component movable relative to the staple cartridge component between spaced apart and approximated positions to adjustably clamp tissue between the staple cartridge and anvil component;
   a buttress member in registration with at least a portion of the plurality of staple pockets defined in the anvil member; and
   a buttress mount secured to the shaft of the anvil component, the buttress mount configured to be received in a recess defined in the anvil member, the buttress mount including at least one support member configured to engage a peripheral edge of the recess of the anvil member to secure the buttress mount within the recess, wherein the buttress mount is attached to a distal surface of the buttress member.

2. The apparatus according to claim 1, wherein the at least one support member is affixed to the buttress member.

3. The apparatus according to claim 1, wherein the buttress mount further includes an annular ring member configured to receive the shaft of the anvil component therethrough, the at least one support member extending radially outward from the annular ring member.

4. The apparatus according to claim 3, wherein the buttress mount is separate from the buttress member, and the buttress mount is detachable from the buttress member.

5. The apparatus according to claim 3, wherein the at least one support member extends linearly outward from the annular ring member.

6. The apparatus according to claim 1, wherein the at least one support member is disposed radially inward of the plurality of staple pockets.

7. The apparatus according to claim 1, wherein the buttress member is made of a biodegradable material.

8. The apparatus according to claim 1, further comprising a knife member movable relative to the staple cartridge component, wherein the at least one support member of the buttress mount is disposed radially inward of the knife member when the knife member engages the buttress member.

\* \* \* \* \*